United States Patent
Li et al.

(10) Patent No.: US 9,155,744 B2
(45) Date of Patent: Oct. 13, 2015

(54) PHARMACEUTICAL COMPOSITION AND METHOD FOR REGENERATING MYOFIBERS IN THE TREATMENT OF MUSCLE INJURIES

(75) Inventors: Ming Li, Hong Kong (CN); Lei Cheng, Hong Kong (CN); Hong Wei Liu, Beijing (CN)

(73) Assignee: Lead Billion Limited, Kowloon Bay, Hong Kong (CN)

( * ) Notice: Subject to any disclaimer, the term of this patent is extended or adjusted under 35 U.S.C. 154(b) by 568 days.

(21) Appl. No.: 11/722,915

(22) PCT Filed: Oct. 27, 2006

(86) PCT No.: PCT/CN2006/002885
§ 371 (c)(1),
(2), (4) Date: Jun. 27, 2007

(87) PCT Pub. No.: WO2007/048352
PCT Pub. Date: May 3, 2007

(65) Prior Publication Data
US 2009/0028959 A1    Jan. 29, 2009

Related U.S. Application Data

(60) Provisional application No. 60/791,462, filed on Apr. 13, 2006.

(30) Foreign Application Priority Data

Oct. 27, 2005 (WO) .................. PCT/IB2005/003191
Oct. 27, 2005 (WO) .................. PCT/IB2005/003202

(51) Int. Cl.
*A61K 31/56* (2006.01)
*A61K 31/704* (2006.01)
*C07C 62/32* (2006.01)

(52) U.S. Cl.
CPC ............... *A61K 31/56* (2013.01); *A61K 31/704* (2013.01); *C07C 62/32* (2013.01)

(58) Field of Classification Search
USPC .......................................................... 514/183
See application file for complete search history.

(56) References Cited

U.S. PATENT DOCUMENTS

| | | | |
|---|---|---|---|
| 5,916,919 A | 6/1999 | Xu et al. | |
| 7,387,801 B2 | 6/2008 | Li et al. | |
| 7,572,467 B2 | 8/2009 | Li et al. | |
| 2005/0064048 A1 | 3/2005 | Li et al. | |

FOREIGN PATENT DOCUMENTS

| | | |
|---|---|---|
| CN | 1582946 A | 2/2005 |
| CN | 1582951 A | 2/2005 |
| CN | 1582952 A | 2/2005 |
| CN | 1608628 A | 4/2005 |
| WO | WO 03/043645 A1 | 5/2003 |
| WO | WO 2004/052381 A1 | 6/2004 |
| WO | WO 2007/048352 A1 | 5/2007 |
| WO | WO 2007/048353 A1 | 5/2007 |
| WO | WO 2007/049088 A1 | 5/2007 |
| WO | WO 2007/049089 A1 | 5/2007 |

OTHER PUBLICATIONS

Remington's Pharmaceutical Sciences, 1980, Chapter 27: Structure-Activity Relationship and Drug Design, pp. 420-435.*
Orlic, D., et al., "Bone marrow cells regenerate infarcted myocardium", Nature, 410, pp. 701-705, (2001).
Toma,C., et al., "Human Mesenchymal Stem Cells Differentiate to a Cardiomyocyte Phenotype in the Adult Murine Heart", Circulation, 105, pp. 93-98, (2002).
Tomita, S., et al., "Autologous Transplantation of Bone Marrow Cells Improves Damaged Heart Function", Circulation, 100, pp. II-247 to II-256, (1999).
Beltrami, A.P., et al., "Evidence that Human Cardiac Myocytes Divide After Myocardial Infarction", New England Journal of Medicine, 344, pp. 1750-1757, (2001).
Kajstura, J., et al., "Myocyte proliferation in end-stage cardiac failure in humans", Proc. Natl. Acad. Sci. USA, 95, pp. 8801-8805, (1998).
Laugwitz, K.L., et al., "Postnatal isl1+cardioblasts enter fully differentiated cardiomyocyte lineages", Nature, 433, pp. 647-653, (2005).
Leferovich, J.M., et al., "Heart regeneration in adult MRL mice", Proc Natl Acad Sci USA, 98, pp. 9830-9835, (2001).

(Continued)

*Primary Examiner* — James D Anderson
*Assistant Examiner* — Meghan Finn
(74) *Attorney, Agent, or Firm* — Jones Day

(57) ABSTRACT

A pharmaceutical composition and method for regenerating cardiomyocytes in treating or repairing heart muscle damages or injuries caused by an ischemic disease. The pharmaceutical composition contains an active ingredient compound with a backbone structure of Formula (I). The active ingredient compound is capable of (a) increasing viability of myogenic precursor cells to enable said precursor cells to survive through an absolute ischemic period; (b) reconstituting a damaged blood supply network in said heart region where said injured muscle is located; and (c) enhancing cardiomyogenic differentiation efficiency of said precursor cells down cardiac linage, said steps being performed simultaneously or in any particular order.

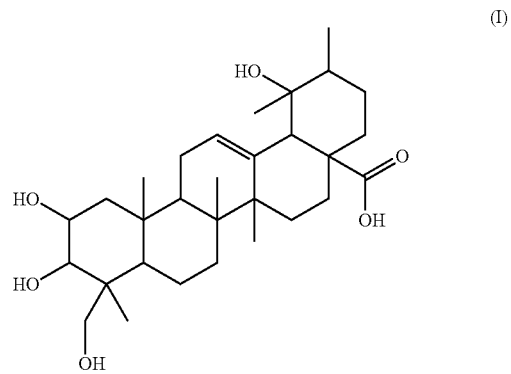

(I)

7 Claims, 7 Drawing Sheets

(56) References Cited

OTHER PUBLICATIONS

Poss, K.D., et al., "Heart Regeneration in Zebrafish", Science, 298, pp. 2188-2190, (2002).
Reinecke, H., et al., "Survival, Integration, and Differentiation of Cardiomyocyte Grafts: A Study in Normal and Injured Rat Hearts", Circulation, 100, pp. 193-202, (1999).
Taylor, D.A., et al., "Regenerating functional myocardium: Improved performance after skeletal myoblast transplantation", Nat Med, 4, pp. 929-933, (1998).
Yoo, K.J., et al., "Heart Cell Transplantation Improves Heart Function in Dilated Cardiomyopathic Hamsters", Circulation, 102, pp. III-204 to III-209, (2000).
Mangi, A.A., et al., "Mesenchymal stem cells modified with Akt prevent remodeling and restore performance of infarcted hearts", Nat Med, 9, pp. 1195-1201, (2003).
Kanegusuku,M., et al., "Cytotoxic Hypoglycemic Activity and Phytochemical Analysis of *Rubus imperialis* (Rosaceae)", Z. Naturforsch., 57(3/4), pp. 272-276, (2002).
Hirai, N., et al.,"Triterpene Phytoalexins from Strawberry Fruit", Bioscience, Biotechnology, and Biochemistry, 64(8),pp. 1707-1712, (2000).
Gazar, H.A., et al., "Iridoids and triterpene saponins from *Verbascum wiedemannianum* (Scrophulariaceae)", Biochemical Systematics and Ecology, 31(4), pp. 433-436, (2003).
Chenchen, Z., et al., "Comparative studies on pharmacological effects of anti-myocardial infraction of different extraction from fruits of *Actinidia rubricaulis* var. Coriacea", Pharmacology and Clinics of Chinese Materia Medica,17(1), pp. 19-21, (2001), Abstract Only Considered.
Search report from corresponding PCT application No. PCT/CN2006/002885.
Aggarwal, "Suppression of the nuclear factor-κB activation pathway by spice-derived phytochemicals," *Ann. N.Y. Acad. Sci* 1030:434-441 (2004).
Andrikopoulos et al., "Biological activity of some naturally occurring resins, gums and pigments against in vitro LDL oxidation," *Phytotherapy Res.*, 17:501-507 (2003).
Assaf, "Phytochemical investigation of *Ocimum basilicum* L. and its hypotensive and cardiovascular activity," *Bull. Pharm. Sci.*, 26(2):201-205 (2003).
Grande et al., "Vasomodulating potential of mediterranean wild plant extracts," *J. Agric. Food Chem.*, 52:5021-5026 (2004).
Huang et al., "Pomegranate flower extract diminishes cardiac fibrosis in zucker diabetic fatty rats," *J. Cardiovasc. Pharmacol.*, 46(6):856-862 (2005).
Kolak et al., "Cardioactive diterpenoids from the roots of *Salvia amplexicaulis*," *Planta Med.*, 67:761-763 (2001).
Shigenaga et al., "Triterpenoids and glycosides from *Geum japonicum*," *Phytochemistry* 24(1):115-118 (1985).
Somova et al., "Cardiovascular, antihyperlipidemic and antioxidant effects of oleanolic and ursolic acids in experimental hypertension," *Phytomedicine*, 10:115-121 (2003).
Xu et al., "Anti-HIV triterpene acids from *Geum japonicum*," *J. Natural Products*, 59(7):643-645 (1996).
Zhang et al., "Characterization of antioxidants present in hawthorn fruits," *J. Nutritional Bioichem.*, 12:144-152 (2001).

\* cited by examiner a b

5

6

7 a b

PHARMACEUTICAL COMPOSITION AND METHOD FOR REGENERATING MYOFIBERS IN THE TREATMENT OF MUSCLE INJURIES

CROSS REFERENCE TO RELATED APPLICATIONS

This application is a §371 national stage application of PCT/CN2006/002885, and claims priority to U.S. Provisional Application No. 60/791,462, filed Apr. 13, 2006, the contents of which are hereby incorporated by reference. The application further claims priority to PCT Application Nos. PCT/IB2005/003202 and PCT/IB2005/003191, both filed Oct. 27, 2005, the contents of which are hereby incorporated by reference.

FIELD OF THE INVENTION

This invention relates to a pharmaceutical composition and a method of regenerating myocytes and myocardium for treating muscle damages. Particularly, it relates to a pharmaceutical composition and method for regenerating cardiomyocytes in treating or repairing heart muscle damages or injuries caused by an ischemic disease.

BACKGROUND OF THE INVENTION

Myocardial infarction (MI), or heart attack, is a disease due to interruption of the blood supply to a part of the heart, causing damage or death of heart muscle cells. It is the leading cause of death for both men and women over the world. Following myocardial infarction, there does not seem to be any natural occurring repairing process capable of generating new cardiomyocytes to replace the lost muscle cells. Instead, scar tissues may replace the necrosed myocardium, causing further deterioration in cardiac function.

Therapeutic replacement of the necrosed heart tissue with newly regenerated functional cardiac myocytes is a treatment ideal that until recently has been unrealistic, because cardiac myocytes were considered to be terminally differentiated, or in other words, the heart is a postmitotic nonregenerating organ. This dogma, however, has recently been challenged by Beltrami et al, and others, who reported that a population of resident myocytes within the myocardia can and do replicate after infarction. In order to promote and improve the repair for infarcted myocardia, transplantation of cardiomyocytes or skeletal myoblasts has been attempted, but has not been very successful in reconstituting functional myocardia and coronary vessels. Transplantation of adult bone marrow-derived mesenchymal stem cells (MSCs) for cardiac repair following myocardial infarction has resulted in some angiogenesis and myogenesis, but the location of the newly regenerated cardiac myocytes appeared mostly along the border zone where the blood supply is relatively less affected[1-3].

Because acute myocardial infarction (MI) brings rapid damages or death to myocytes (heart muscle cells), vascular structures and nonvascular components in the supplied region of the ventricle, regeneration of new cardiac myocytes to replace the infarcted myocardia (heart muscular tissues) in the central infarcted zone (the absolute ischemic region) through a sub-population of cardiac myocyte growth[4-8] or transplantation of MSCs[1-3] alone appears to be impossible without early reestablishment of the blood supply network locally. This probably explains why regeneration of cardiac myocytes following MSCs transplantation alone occurred mostly along the border zone adjacent to the infarct where the blood supply is largely maintained[1-11]. Therefore, the loss of myocardia, arterioles and capillaries in the central infarct area appeared to be irreversible, eventually leading to scar formation.

A more recent study[12] reported that heart transplantation of MSC pre-modified with exogenous Akt in vitro produced a better result. Nonetheless, the regenerated cardiac myocytes could only infiltrate from the border zone into the scarred area, indicating that overexpression of exogenous Akt, although enhancing the survival potential of the transplanted MSCs, itself is insufficient to enable them to survive in central ischemic regions. Furthermore, even in the less-ischemic border zones, it was noted that the MSCs-derived regenerating cardiac myocytes were scattered and seemed to have difficulty to cluster and form regenerating myocardia. This is probably due to poor cardiomyogenic differentiation efficiency of the survived transplanted MSCs. The knowledge that natural cardiomyocyte reproduction, including differentiation of residential progenitor myocytes or stem cells recruited from other sources, such as from endothelial cells or a niche in the bone marrow is insufficient to balance cardiomyocyte death occurred in acute or chronically damaged heart, has damped the enthusiasm of the researchers who thought myocardial regeneration would represent a promising method of treatment against heart diseases.

The prior art seems to teach that there are three major requirements critical for regenerating functional myocytes in the entire areas of infarcted myocardia: 1) increased viability of the transplanted cells so that they may survive through the absolute ischemic period, that is, the period from injection of the donor cells to formation of new vessels; 2) early reconstitution of the damaged blood supply network in the infarcted myocardia to sustain the survival and efficient trafficking of the transplanted cells and maintain oxygenation and nutrient delivery; and 3) enhanced cardiomyogenic differentiation efficiency of the transplanted cells to enable more survived donor cells to differentiate down cardiac linage.

Therefore, to realize the therapeutic ideal of replacing necrosed heart tissues with newly regenerated functional cardiac myocytes, there is a need for new therapeutic approaches, for example, an approach using chemical compounds possessing biological properties that sufficiently satisfy the aforementioned three requirements in order to serve the therapeutic needs for treating myocardial infarction.

SUMMARY OF THE INVENTION

As one object of the present invention, there is provided a pharmaceutical composition comprising a compound selected from the group of chemical compounds sharing a common backbone structure of formula (I). The compounds have potent beneficial therapeutic effects not only on the survival potential and cardiogenic differentiation efficiency of MSCs ex vivo, but also on repairing of MI in vivo. These compounds themselves are known in the art but they are never known as possessing the above biological activities and therapeutic effects. They may be isolated from natural resources, particularly from plants or they may also be obtained though total or semi-chemical syntheses, with existing or future developed synthetic techniques. The backbone structure itself possesses the aforementioned myogenic effects and various variants can be made from the backbone structure through substitution of one or more hydrogen atoms at various positions. These variants share the common backbone skeleton and the myogenic effects. Of course, they may vary in myogenic potency.

Formula (I)

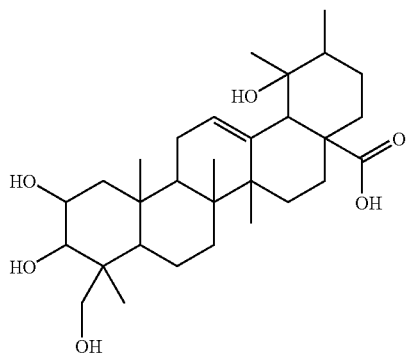

The backbone structure of Formula (I) may have one or more substituents attached. A substituent is an atom or group of atoms substituted in place of the hydrogen atom. The substitution can be achieved by means known in the field of organic chemistry. For example, through a proper design, high through-put combinatorial synthesis is capable of producing a large library of variants or derivatives with various substituents attached to various positions of a backbone structure. The variants or derivatives of formula (I) may then be selected based on an activity test on mesenchymal stem cells (MSCs), which can quickly determine whether a particular variant could enhance proliferation and cardiogenic differentiation of the cultured MSCs. As used in this application, the term "the compound of formula (I)" encompasses the backbone compound itself and its substituted variants with similar biological activities. Examples of these variants are presented in the following, all of which possess similar effects in terms of regenerating functional myocytes as the backbone structure (i.e., the base compound itself):

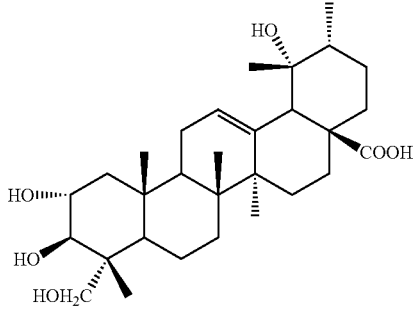

2α, 3β, 19α, 23-tetrahydroxy urs-12-en-28-oic acid

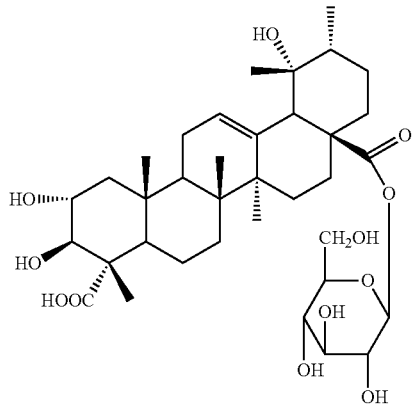

Suavissimoside R1

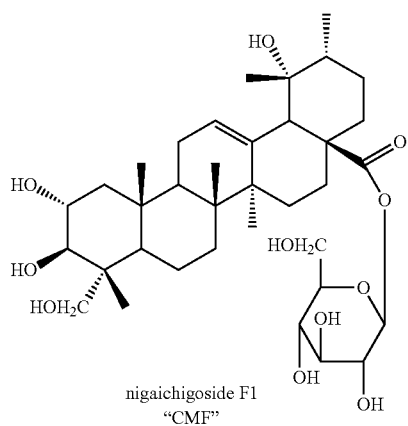

nigaichigoside F1 "CMF"

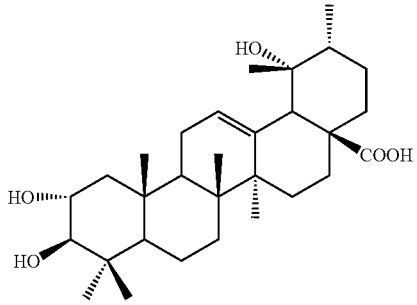

Tormentic acid

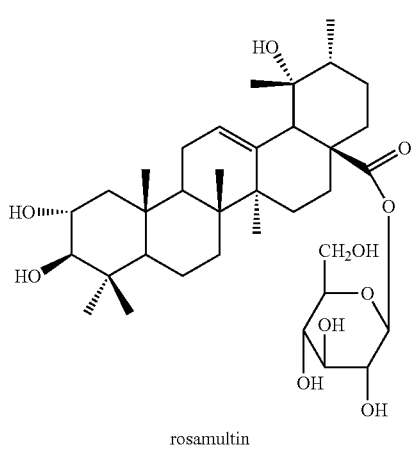

rosamultin

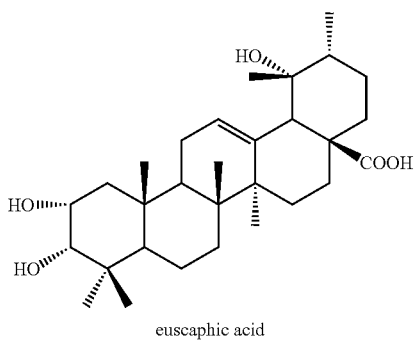

euscaphic acid

Furthermore, as a therapeutic agent, the compound of formula (I) may be in a form of "functional derivatives" as defined below.

It is contemplated, as a person with ordinary skill in the art would contemplate, that the above compounds may be made in various possible racemic, enantiomeric or diastereoisomeric isomer forms, may form salts with mineral and organic acids, and may also form derivatives such as N-oxides, prodrugs, bioisosteres. "Prodrug" means an inactive form of the compound due to the attachment of one or more specialized protective groups used in a transient manner to alter or to eliminate undesirable properties in the parent molecule, which is metabolized or converted into the active compound inside the body (in vivo) once administered. "Bioisostere" means a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Making suitable prodrugs, bioisosteres, N-oxides, pharmaceutically acceptable salts or various isomers from a known compound (such as those disclosed in this specification) are within the ordinary skill of the art. Therefore, the present invention contemplates all suitable isomer forms, salts and derivatives of the above disclosed compounds.

As used in this application, the term "functional derivative" means a prodrug, bioisostere, N-oxide, pharmaceutically acceptable salt or various isomer from the above-disclosed specific compound, which may be advantageous in one or more aspects compared with the parent compound. Making functional derivatives may be laborious, but some of the technologies involved are well known in the art. Various high-throughput chemical synthetic methods are available. For example, combinatorial chemistry has resulted in the rapid expansion of compound libraries, which when coupled with various highly efficient bio-screening technologies can lead to efficient discovering and isolating useful functional derivatives.

The pharmaceutical composition of the present invention is useful for treating myocardial injuries or necrosis caused by a disease, particularly MI, through regenerating heart tissues. The pharmaceutical composition may be formulated by conventional means known to people skilled in the art into a suitable dosage form, such as tablet, capsule, injection, solution, suspension, powder, syrup, etc, and be administered to a mammalian subject having myocardial injuries or necrosis. The formulation techniques are not part of the present invention and thus are not limitations to the scope of the present invention.

The pharmaceutical composition of the present invention may be formulated in a way suitable for oral administration, systemic injection, and direct local injection in the heart or implantation in a body part for long-term slow-releasing.

In another aspect, present invention provide a method for treating or ameliorating a pathological condition in a mammal, where the pathological condition, as judged by people skilled in medicine, can be alleviated, treated or cured by regenerating functional cardiomyocytes and where the method comprises administering to the mammal with the pathological condition a therapeutically effective amount of a compound of formula (I) and or its functional derivatives.

In another aspect, the present invention provides a method of regenerating functional cardiomyocytes in a mammal who needs to replace dead or damaged heart tissues caused by a heart disease, such as, myocardial infarction (MI). This is a cell-transplantation based therapeutic approach, involving the steps of: (a) obtaining stem cells, such as MSCs; (b) contacting the stem cells with a compound of the formula (I) or their functional derivatives to activate the pathways of cardiogenic differentiation prior to transplantation and (c) then transplanting the activated cells into the infarcted heart tissues of the mammal. This therapeutic approach is capable of achieving the following goals: 1) enhanced survival potential of the transplanted cells; 2) early reconstitution of blood supply network, and 3) enhanced cardiomyogenic differentiation efficiency of the transplanted cells by ex vivo activation of MSCs forming cardiogenic progenitors prior to transplantation.

In another aspect, the present invention provides a method for treating ischemic heart diseases, particularly MI in mammals, which comprising the steps: (a) culturing MSCs or endothelial cells with a compound of formula (I) or their functional derivatives, (b) gathering the conditioned medium of the treated cells, which contains secretary proteins that are active in driving heart infarction repair or cardiogenic differentiation of MSCs, and (c) administering or delivering the conditioned medium to the heart tissue in the infarct area.

In still another aspect, the present invention provides a research reagent for scientific research on cardiogenic trans-differentiation of stem cells, such as MSCs. The reagent comprises one or more compounds of formula (I) or their functional derivatives. It may be in a solid form or a liquid form. For example, it may be a solution of DMSO.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS

I. Experiment Procedures

All protocols used in the present invention conformed to the Guide for the Care and Use of Laboratory Animals published by the U.S. National Institutes of Health, and were approved by the Animal Experimental Ethical Committee of The Chinese University of Hong Kong.

For the following discussion, CMF refers to nigaichigoside F1. Its chemical structure is defined as shown above.

Obtaining Compounds of the Present Invention: The compounds can be prepared from plants, although it may possible to make it through chemical synthesis.

As an example for illustrating the process of preparing the compounds from natural resources, the following provides details involved in CMF's isolation and purification from one plant species, *Geum Japonicum*. Other plants that may contain CMF or variants include, for example, *Acaena pinnatifida R. et P., Agrimonia pilosa Ledeb, Asparagus filicinus, Ardisia japonica, Campsis grandiflora, Campylotropis hirtella* (Franch. Schindl.), *Caulis Sargentodoxae, Cedrela sinensis, Chaenomeles sinensis KOEHNE, Debregeasia salicifolia, Eriobotrya japonica calli, Eriobotrya japonica LINDL.* (Rosaceae), *Goreishi, Leucoseptrum stellipillum, Ludwigia octovalvis, Perilla frutescens, Perilla frutescens* (L.) Britt. (Lamiaceae), *Physocarpus intermedius Potentilla multifida L., Poterium ancistroides, Pourouma guianensis* (Moraceae), *Rhaponticum uniflorum, Rosa bella Rehd. et Wils., Rosa laevigata Michx, Rosa rugosa, Rubus alceaefolius Poir, Rubus allegheniensis, Rubus coreanus, Rubus imperialis, Rubus imperialis Chum. Schl.* (Rosaceae), *Rubus sieboldii, Rumex japonicus, Salvia trijuga Diels, Strasburgeria robusta, Strawberry* cv. *Houkouwase, Tiarella polyphylla, Vochysia pacifica Cuatrec, Zanthoxylum piperitum*, etc.

Figure 1:
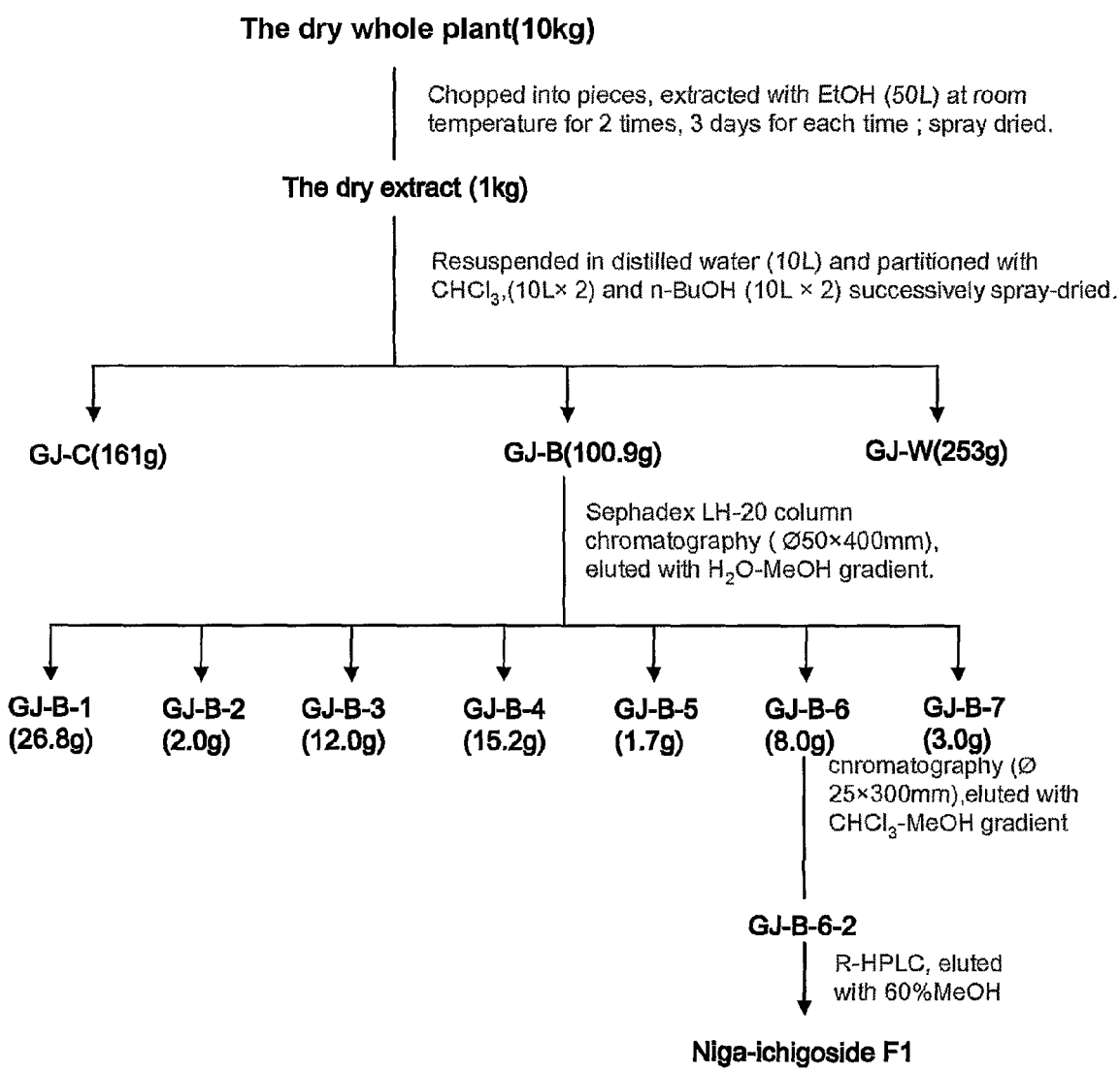
FIG. 1 outlines the process of isolating Niga-ichigoside F1 (referred to as "CMF") from the plant of *Geum Japonicum* as an example of making the compound of the present invention.

Isolation of cardiomyogenic factor (CMF) from *Geum japonicum*: Referring to FIG. 1, the plant of *Geum japonicum* collected from Guizhou Province of China in August was dried (10 kg) and percolated with 70% ethanol (100 L) at room temperature for 3 days twice. The extract was combined and spray-dried to yield a solid residue (1 kg). The solid residue was suspended in 10 liter $H_2O$ and successively partitioned with chloroform (10 L) twice, then n-butanol (10 L) twice to produce the corresponding fractions. The n-butanol (GJ-B) soluble fraction was filtered and dried by spray drying to yield a powder fraction, which was confirmed for their specific ability to stimulate cardiogenic differentiation of MSCs in cell culture in a way described below. It was shown that n-butanol soluble fraction GJ-B) could enhance the proliferation and cardiogenic differentiation of the cultured MSCs in cell culture systems. The GJ-B fraction was then applied on a column of Sephadex LH-20 equilibrated with 10% methanol and eluted with increasing concentration of methanol in water, resolving 7 fractions, GJ-B-1 to GJ-B-7. All the eluted fractions were tested for their activity with MSC culture systems. Activity test demonstrated that fraction 6 was most active in enhancing the cardiogenic differentiation of cultured MSCs. From GJ-B-6, a pure active compound was further isolated, which is referred to as CMF or nigaichigoside F1 through this disclosure. CMF's structure was determined by NMR analysis and comparison with literature, and shown to be as above for nigaichigoside F1.

Preparation of MSCs for transplantation: The MSCs were cultured with CMF (10 µg/ml in growth medium) for 6 days. In parallel, the control MSCs were cultured in growth medium containing equivalent volume of 5% DMSO. On day 2, expression of endogenous phospho-Akt1 was assessed by immunocytochemistry and Western blot. On day 4, myogenic differentiation was assessed by immunocytochemistry and Western blot against MEF2, which were further confirmed by immunocytochemistry and Western blot with an antibody specific to MHC on day 6. On day 3, both the CMF-pretreated MSCs and the control MSCs were labeled with CM-DiI in culture and made ready for transplantation.

Preparation of bone marrow mesenchymal stem cells: The tibias/femur bones were removed from Sprague-Dawley (SD) rats and the bone marrow (BM) was flushed out of the bones with IMDM culture medium containing 10% heat inactivated FBS (GIBCO) and 1% penicillin/streptomycin. The BM was thoroughly mixed and centrifuged at 1500 rpm for 5 minutes. The cell pellet was suspended in 5 ml growth medium. The cell suspension was carefully put on 5 ml Ficoll solution and centrifuged at 200 rpm for 30 min. The second layer, which contains BM cells was transferred into a tube and washed twice with PBS to remove Ficoll (1200 rpm for 5 minutes). The cell pellet was resuspended in IMDM culture medium containing 10% heat inactivated FBS (GIBCO) and 1% penicillin/streptomycin antibiotic mixture. After 24 hours culture in a 37° C. incubator with 5% $CO_2$, the non-adherent cells are discarded and the adherent cells are cultured by changing medium once every 3 days and the cells became nearly confluent after 14 days of culture. This was the BM cells, referred to as MSCs in the following, which were used for in vitro and in vivo studies conducted in the present disclosure.

Western blot analysis. Whole cell extracts of the CMF-treated cells or control cells were prepared by lysing the cells with 3 times packed cell volume of lysis buffer (50 mM Tris, pH 7.5, 150 mM NaCl, 1 mM EDTA, 1 mM EGTA, 1% Nonidet P-40, 10% glycerol, 200 mM NaF, 20 mM sodium pyrophosphate, 10 mg/ml leupeptin, 10 mg/ml aprotinin, 200 mM phenylmethylsulfonyl fluoride, and 1 mM sodium orthovanadate) on ice for 30 minutes. Protein yield was quantified by Bio-Rad DC protein assay kit (Bio-Rad). Equal amounts (30 µg) of total protein were size-fractionated by SDS-PAGE and transferred to PVDM membranes (Millipore). The blots were blocked with phosphate-buffered saline plus 0.1% (vol/vol) Tween 20 (PBST) containing 5% (wt/vol) milk powder (PBSTM) for 30 minutes at room temperature and probed for 60 minutes with specific primary antibodies against rat phospho-Akt1 (mouse) or rat MHC (mouse, Sigma-Aldrich), diluted 1:1000 in PBSTM. After washing extensively in PBST, the blots were probed by horseradish peroxidase-coupled anti-mouse IgG (Amersham Biosciences) (1/1000 dilution in PBSTM, 60 min), extensively washed with PBST, and developed by chemiluminescence.

Transplantation of the CMF-pretreated MSCs to the heart tissue: The Sprague-Dawley (SD) rats were used and all animal procedures were approved by the University Animal Committee on Animal Welfare. Each rat was anesthetized with intraperitoneal pentobarbital (50 mg/kg), intubated, and mechanically ventilated with room air using a Harvard ventilator (model 683). After a left thoracotomy, myocardial infarction was induced by permanent ligation of left anterior descending (LAD) coronary artery. The $5 \times 10^5$ DiI labeled CMF-pretreated MSCs (32 rats) suspended in saline were injected into three sites of the distal myocardia (the ischemic region) of the ligated artery immediate after the ligation respectively (test group). The control rats were injected with an equivalent amount of DiI labeled non-treated control MSCs (32 rats) suspended in saline at the same location and timing. For sham ischemia (32 rats), thoracotomy was performed without LAD ligation. Sixteen rats subject to no-treatment were set as normal control.

Half of the experimental rats from different groups were sacrificed according to experimental plan on day 7 and day 14 post-infarction after assessment of their heart function by echocardiography measurements. The hearts of the sacrificed rats were removed, washed with PBS and photographed respectively. All the specimens harvested were paraffin embedded and sectioned for tracing the signals of DiI and examination of revascularization, infarct size and regeneration of myocardia. If the regenerating cells were DiI positive, further MHC immonohistochemical staining was performed to confirm their cardiomyogenic differentiation.

Colocalization of the DiI label and cardiac-specific marker expression were examined with a confocal microscope (ZEISS, LSM 510 META). Briefly, the sections were immunohistochemically stained with rat-specific troponin I antibodies. The confirmation of cardiomyogenic differentiation of the DiI labeled transplanted MSCs forming regenerating myocardia was carried out by merging the DiI-positive cells, indicating their donor cell origin, with the specific positive staining of cardiac terminal differentiation marker-troponin I using confocal microscopic examination, implying their cardiomyogenic differentiation of these transplanted cells.

CMF direct treatment in MI model: Thirty-two SD rats were randomly divided into four groups: normal group, sham group, CMF-treated group and non-treated control group (8 rats each). Rats were anesthetized with intraperitoneal pentobarbital (50 mg/kg), intubated, and mechanically ventilated with room air using a Harvard ventilator (model 683). After a left thoracotomy, myocardial infarction was induced by permanent ligation of left anterior descending (LAD) coronary artery. CMF in 5% DMSO (0.1 ml, containing 0.1 mg CMF) was injected into the distal myocardium (the ischemic region) of the ligated artery in 8 rats immediate after the ligation (CMF-treated group). Another 8 rats were injected with an equivalent amount of 5% DMSO at the same location and timing as non-treated control group. For sham ischemia, thoracotomy was performed on 8 rats without LAD ligation. Further 8 rats without any treatment were set as normal group.

Conditioned medium containing secretary proteins from MSCs or other cells induced by CMF: The MSCs were treated with 10 ug/ml CMF for 24 hours to activate/upregulate gene expressions and then washed thoroughly to remove residue of CMF. Then 5 ml of fresh growth medium was added to the culture and collected after another 3 days of culturing. The collected medium was referred to as conditioned medium. The 5 ml of conditioned medium was condensed to a volume of 1 ml, and was used as a treatment agent in the heart infarction animal model as described above. Briefly, after a left thoracotomy and ligation of LAD, 0.2 ml of the conditioned medium was injected immediately into the distal part of ligation. Fresh growth medium was used as control.

Bone marrow replacement with DiI labeled MSCs: Sixteen 5-week old SD rats were used for bone marrow transplantation. Recipient rats were irritated by 9.5 Gy of gamma irradiation from a 137Cs source (Elite Grammacell 1000) at a dosage of 1.140 Gy/min to completely destroy the bone marrow derived stem cells of the rat. DiI-labeled MSCs ($2 \times 10^8$ cells suspended in 0.3 ml PBS) were then injected through tail vein within 2 hours after irritation using a 27-gauge needle. One week after irritation and transplantation, the rats with DiI-labeled bone marrow were divided into two groups: one to be treated directly with CMF and the other as control without treatment. Heart infarction surgery and treatment scheme were performed as described above. The experiment was terminated on day 14 post surgery and treatment for further assessment. Heart specimens of the sacrificed rats were obtained. All the specimens were traced for DiI positive cells and their cardiomyogenic differentiation by immunohistochemical staining with specific antibodies for heart type troponin I (Santa Cruz) and PCNA (Dako). Specific secondary antibody conjugated with alkaline phosphatase (Santa Cruz) was used to visualize the positively stained cells. DiI positive signal was observed with a fluorescence microscope (Laica)

Estimation of infarct size: Left ventricles from experimental rats sacrificed on day 14 were removed and sliced from apex to base in 3 transverse slices. The slices were fixed in formalin and embedded in paraffin. Sections (20 µm thickness) of the left ventricle were stained with Masson's trichrome, which labels collagen blue and myocardium red. These sections were digitized and all blue staining was quantified morphometrically. The volume of infarct ($mm^3$) of a particular section was calculated based on the thickness of the slice. The volumes of infarcted tissue for all sections were added to yield the total volume of the infarct for each particular heart. All studies were performed by a blinded pathologist.

Angiogenic assessment in infarct region: Vascular density was determined on day 7 postinfarction from histology sections by counting the number of vessels within the infarct area using a light microscope under high power field (HPF) (×400). Six random and non-overlapping HPFs within the infarct filed were used for counting all newly formed vessels in each section of all experimental hearts. The number of vessels in each HPF is averaged and expressed as the number of vessels per HPF.

Assessment of regenerating cardiac myocytes and myocardia: The sections from both CMF pretreated MSCs-transplanted and non-treated MSCs-transplanted groups on day 7 post-ligation were stained with Ki67 or myosin heavy chain (MHC) antibodies to identify the regenerating myocardia. Specific secondary antibody conjugated with alkaline phosphatase was used to visualize the positive stains. Briefly, paraffin-embedded sections were microwaved in a 0.1 M EDTA buffer and stained with a polyclonal rabbit antibody with specificity against rat Ki67 at 1:3,000 dilution (Sant Cruz Biotechnology) and incubated overnight at 4° C. After they were washed, the sections were incubated with a goat anti-rabbit IgG secondary antibody conjugated with alkaline phosphatase at 1:200 dilution (Sigma) for 30 min, and the positive nuclei were visualized as dark blue with a 5-bromo-4-chloro-3-indolylphosphate-p-toluidine-nitro blue tetrazolium substrate kit (Dako). The immediate neighbor sections from corresponding paraffin tissue block were incubated overnight at 4° C. in a 1:50 dilution of rabbit anti-rat MHC (MF20, Developmental Hybridoma Bank, University of Iowa) antibodies, and further incubated for 30 minutes at room temperature in a 1:100 dilution of peroxidase-conjugated goat anti-rabbit IgG (Sigma). After incubation with 1 mg/ml 3,3'-diaminobenzidine (DAB; plus 0.02% $H_2O_2$), the slides were investigated by microscopic analysis. The regenerating myocardium area was delineated in the projected field by a grid containing 42 sampling points. Approximately, 30-60 calculating points along the border of a particular regenerating myocardium were selected in each section. This grid defined an uncompressed tissue area of 62,500 µm², which was used to measure the selected 30-60 calculating points in each section. The shapes and volumes of regenerating myocardia in the central area of infarct were determined by measuring in each section (50 µm apart) of approximately 70 sections the shapes and areas occupied by the regenerating myocardia and section thickness. Integration and calculation with these variables produced a stereo-structure and yields the volume of a particular regenerating myocardium in the central area of the infarct in each section. Values and stereo structure of all sections of a particular tissue block were added and computed to obtain the total volume and the full stereo-structure of the regenerating myocardia.

Echocardiography assessment of myocardial function: Echocardiographic studies were performed using a Sequoia C256 System (Siemens Medical) with a 15-MHz linear array transducer. The chest of experimental rats was shaved, the animal was situated in the supine position on a warming pad, ECG limb electrodes were placed, and echocardiography was recorded under controlled anesthesia. Each experimental rat received a baseline echocardiography before the experimental procedure. Two-dimensional guided M-mode and two-dimensional (2D) echocardiography images were recorded from parasternal long- & short-axis views. Left ventricular (LV) end-systolic and end-diastolic dimensions, as well as systolic and diastolic wall thickness were measured from the M-mode tracings by using the leading-edge convention of the American Society of Echocardiography. LV end-diastolic (LVDA) and end-systolic (LVSA) areas were planimetered from the parasternal long axis and LV end-diastolic and end-systolic volumes (LVEDV and LVESV) were calculated by the M-mode method. LV ejection fraction (LVEF) and fractional shortening (FS) were derived from LV cross-sectional area in 2D short axis view: EF=[(LVEDV−LVESV)/LVEDV]×100% and FS=[(LVDA−LVSA)/LVDA]×100%. Standard formulae were used for echocardiographic calculations. All data were analyzed offline with software resident on the ultrasound system at the end of the study. All measured and calculated indexes were presented as the average of three to five consecutive measurements.

Statistics: All morphometric data are collected blindly, and the code is broken at the end of the experiment. Results are presented as mean±SD computed from the average measurements obtained from each heart. Statistical significance for comparison between two measurements is determined using the unpaired two-tailed Student's t test. Values of P<0.05 are considered to be significant.

Figure 2:
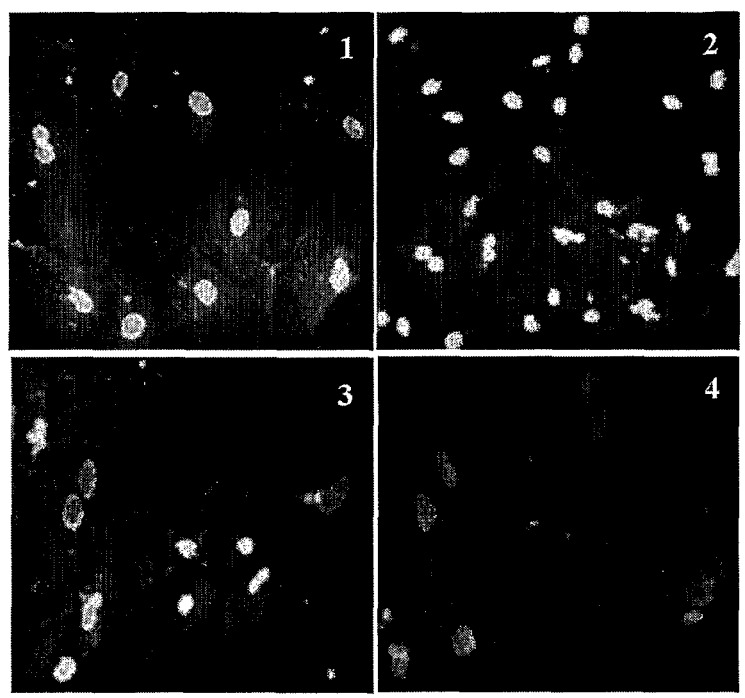
FIG. 2 shows the effects of CMF on cardiogenic differentiation of the MSCs and up-regulation of phospho-Akt1 expression ex vivo.
Figure 2:
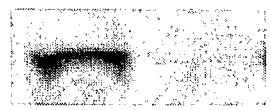
Figure 2:
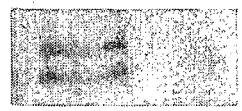
Figure 2:

II. CMF-induced Increased Survival Potential and Cardiogenic Differentiation of MSCs ex vivo Referring to FIG. 2, following two days treatment with CMF (10 µg/ml) in the culture, the expression of phospho-Akt1 was significantly up-regulated compared with the untreated control as demonstrated by immunocytochemical red mainly in the cytoplasm (FIG. 2a: 1). Western blot confirmed that the increased expression of phospho-Akt1 up to 3-4 folds over untreated cells (FIG. 2b: 5A). Among the phospho-Akt1 up-regulated MSCs, more than 90% of them when cultured for 2 additional days became positively stained with the antibody specific to myocyte enhancer factor 2 (MEF2), one of the earliest markers for the cardiogenic lineage, positive cells being stained orange in the nuclei (FIG. 2a: 2) and confirmed by Western blot (FIG. 2b: 6A), indicating their commitment to cardiogenic differentiation. It was noted that the cultured MSCs were not all positively stained by anti-MEF2 antibody (FIG. 2a: 2), as indicated by the blue nucleus possibly because not all cultured MSCs were converted down the cardiogenic differentiation pathway by CMF or because some minor impurities existed in the preparation of MSCs. Similarly, most of the cultured MSCs were positively stained with the antibody specific to heart type myosin heavy chain, positive cells being stained red in the cytoplasm (FIG. 2a: 3) and confirmed by Western blot (FIG. 2b: 7A) upon 6 days culture in the presence of CMF, while control cells were negative stained by all three specific antibodies (FIG. 2a:4 & 2b: Bs). The sequential induction of MEF2 and MHC expressions confirmed the CMF-induced cardiogenic differentiation development of MSCs ex vivo. In FIG. 2b, A stands for CMF-treated sample while B for untreated control.

III. Therapeutic Effect via Transplantation of MSCs Pre-treated with CMF

Figure 3:
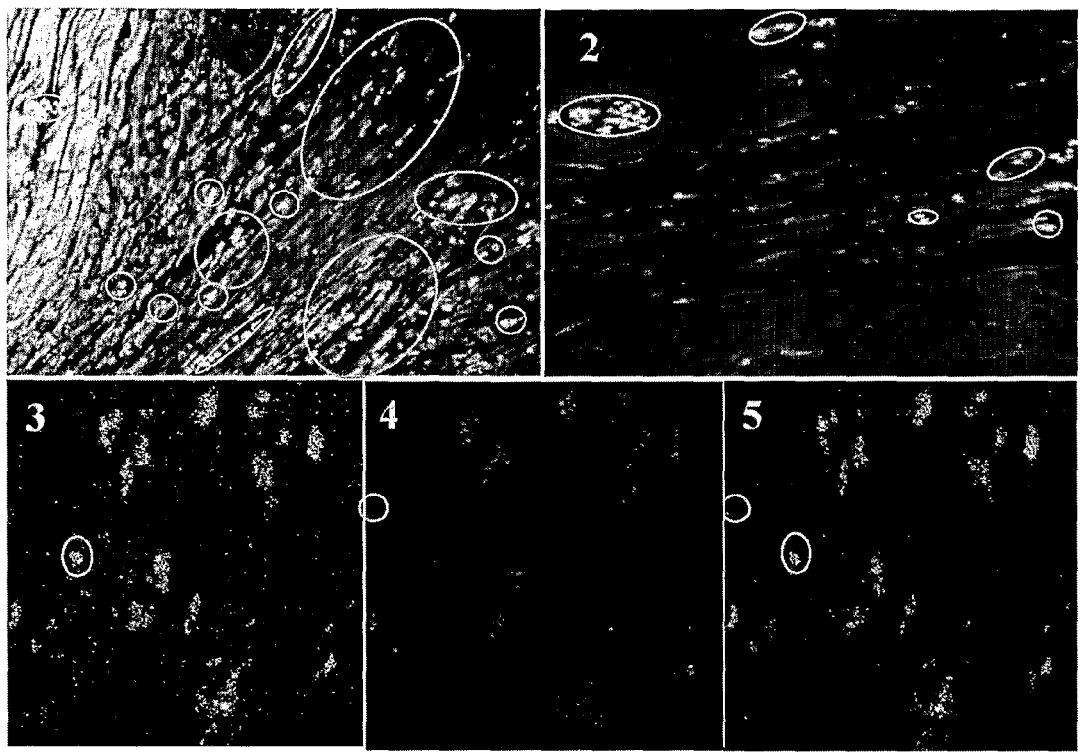
FIG. 3 shows the therapeutic effect of a treatment based on transplantation of CMF-pretreated MSCs.
Figure 3:
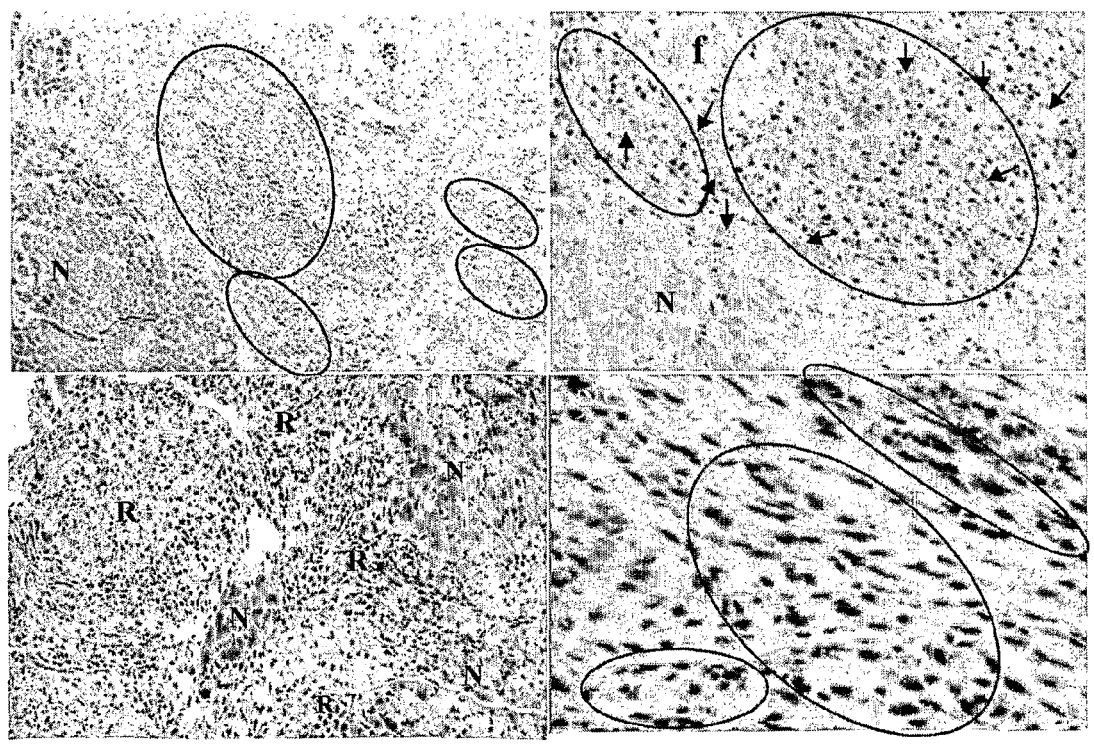

To determine whether the increased survival potential and cardiogenic differentiation efficiency showed ex vivo in MSCs treated with CMF prior to transplantation would bring about significant improvement in repairing of MI in vivo, or in other words, whether CMF's ex vivo effects have any therapeutic values, cell transplantation experiments with MI animal model were performed, where MSCs pre-treated with CMF were implanted in the areas of infarct. The homing, survival, proliferation, cardiomyogenic differentiation and maturation of the transplanted cells were traced by the positive signals of either DiI-florescence and by immunohistochemical staining for Ki67 and MHC in sections, which were from the hearts on day 7 and day 14 post infarction and cell transplantation. As shown in FIG. 3, DiI positive cells on day 7 (FIG. 3: 1) with the characteristic phenotype of a cardiac myocyte were observed in the whole area of the infarct in the test myocardium group, indicating their donor cell origin and whole infarct zone distribution. In control group (untreated with CMF), only scattered DiI signals around the infarct border could be seen (FIG. 3: 2). The colocalization of DiI signals (red) and cardiac specific troponin I expression (green) was observed (FIG. 3: 3-5) in the whole infarct zone by confocal microscopy. The merged image of DiI-positive (red) and cardiac specific marker troponin I expression (green) resulted in yellow-red-green overlapping colors in the same cells, thus confirming the in vivo cardiomyogenic differentiation and maturation of the transplanted MSCs pretreated ex vivo with CMF. It was also noted that a few troponin I positive cells (green) were not DiI positive (FIG. 3: 3 & 5), probably because some regenerating myocytes were not derived from the transplanted DiI-labeled-MSCs. Similarly, a few DiI positive cells shown in the light blue circles (FIG. 3: 4 & 5), were negative in troponin I immunostaining, indicating a small fraction of the transplanted cells did not commit cardiogenic differentiation in vivo, or impurities contained in the preparation of MSCs.

Formation of new vessels could be detected as early as 12 hours after transplantation and many more newly formed vessels and capillaries filled with blood cells were observed in the whole infarct areas in the test group in 24 hours (before any regenerating cardiac myocytes could be seen) and in 7 days post infarction (FIG. 3: 1, yellow circles). The density of the newly formed vessels in the infarct area of the CMF pretreated MSCs transplanted myocardia was on average 8±2 per high power field (40×) (HPF) on day 7. However, the new vessels were not DiI-positive, indicating that the cellular source of the vessels may not be derived from the donor cells. It is contemplated that the donor MSCs may be activated by CMF-pretreatment to stimulate and upregulate angiogenesis specific signaling pathways that induce the expression of certain angiogenic factors, which directly enhances the process of early revascularization in infarcted myocardia. By contrast, approximately 3±2 vessels per HPF were observed in the infarcted myocardia of non-pretreated MSCs transplantated controls on day 7 (FIG. 3: 2, yellow circles).

Figure 4:
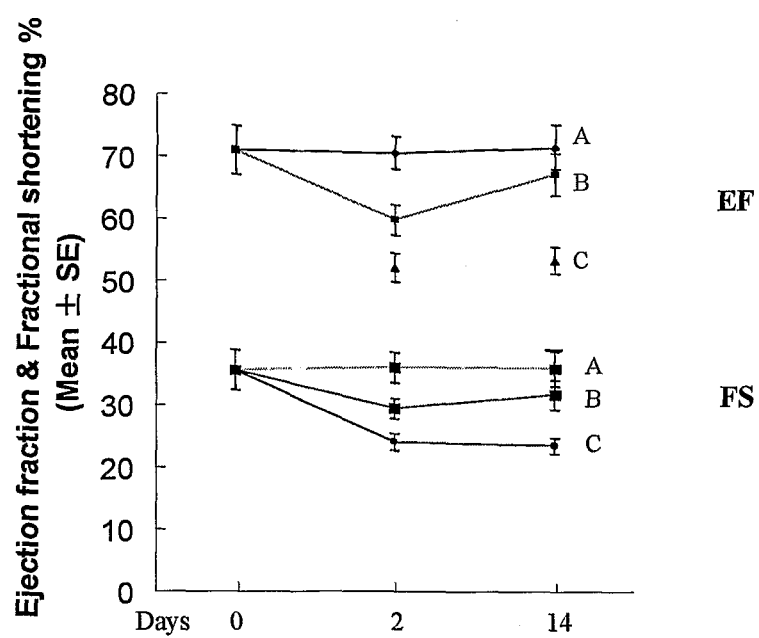
FIG. 4 shows distribution ejection fraction (EF) and fractional shortening (FS) after 2 days and 2 weeks cell transplantation in three groups of rats (A: normal group; B: MI group transplanted with CMF-treated MSCs; C: MI group transplanted with MSCs not treated with CMF).

As shown in FIG. 3, a large number of donor cell derived myocytes were clustered and organized into myocardial-like tissue in the infarct area, which were positively stained by antibodies specific to MHC (FIG. 3: 6, blue circles) and Ki67 (FIG. 3: 7, blue circles), indicating that these transplanted CMF-pretreated MSCs retained the division ability and committed cardiomyogenic differentiation after transplantation in vivo. Under a high power field, these myocardial-like tissues showed the typical morphology of myocardium, except the size was smaller than undamaged existing myocytes (FIG. 3: 9, blue circles). These highly organized regenerating myocardium-like tissues occupied averagely 70±8% of the total infarct volume on day 7 and replaced the infarcted myocardia by 80±8.5% on average on day 14 post-infarction in the test myocardium group (FIG. 3: 8, R, regenerated cardiac myocytes; N, preexisting normal cardiac myocytes). This replacement of the infarcted heart tissue was accompanied by significant functional improvement, as demonstrated in the echocardiography measurements (FIG. 4 & Table 1). In comparison with the non-pretreated MSCs transplanted MI group on day 2 and 14 post infarction, ejection fraction (EF) of the pretreated-MSCs-transplanted MI hearts was significantly higher (59.79±2.33 vs 52.1±2.54, P=0.03) on day 2, and markedly increased (67.13±2.53 vs 53.3±2.31, P=0.001) on day 14. Similarly, fraction shortening (FS) of the transplanted MI heart were significantly higher (29.43±1.35 vs 24.07±1.47, P=0.01) on day 2 and was significantly increased (31.72±2.57 vs 23.49±1.99, P=0.002) on day 14. The significant improvements in EF and FS are a solid reflection of the functional recovery of the cardiac myocytes (Table 1).

TABLE 1

The distribution of ejection fraction (EF) and fractional shortening (FS).
(mean ± _SE):

| | EF (%) | | FS (%) | |
|---|---|---|---|---|
| | 2 days§ | 14 days♪ | 2 days§ | 14 days♪ |
| Normal (16) | 71.03 ± 4.05 | 68.24 ± 4.79 | 35.65 ± 3.99 | 34.02 ± 3.27 |
| Sham (32) | 70.45 ± 2.67 | 71.34 ± 2.77 | 36.03 ± 2.76 | 35.86 ± 2.13 |
| CMF-pretreated (32) | 59.79 ± 2.33* | 67.13 ± 2.53* | 29.43 ± 1.35* | 31.72 ± 2.57* |
| MSC control (32) | 52.1 ± 2.54 | 53.3 ± 2.31 | 24.07 ± 1.47 | 23.49 ± 1.99 |

§Sixteen rats for normal group and 32 rats for sham operated, CMF-pretreated and MSC control groups respectively.
♪Eight rats for normal group and 16 rats for sham operated, CMF-pretreated and MSC control groups respectively.
*EF, P = 0.03 on day 2; P = 0.001 on day 14, and FS, P = 0.01 on day 2 and P = 0.002 on day 14.

Figure 5:
FIG. 5 shows the therapeutic effects of CMF on myocardial infarction (MI) animal model.
Figure 5:
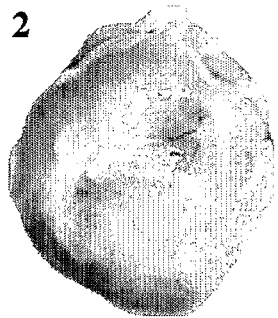
Figure 5:
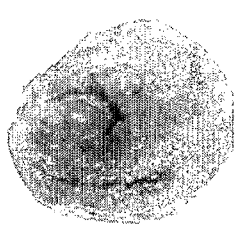
Figure 5:
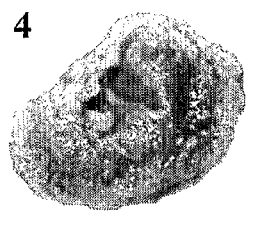
Figure 5:
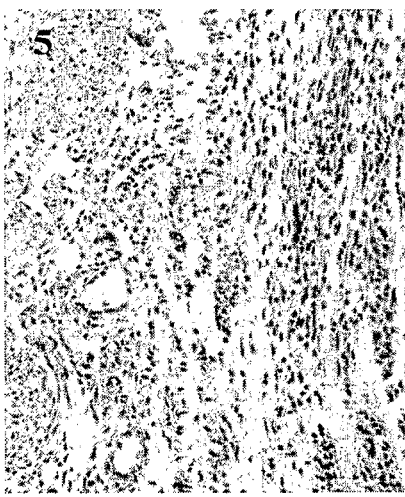
Figure 5:
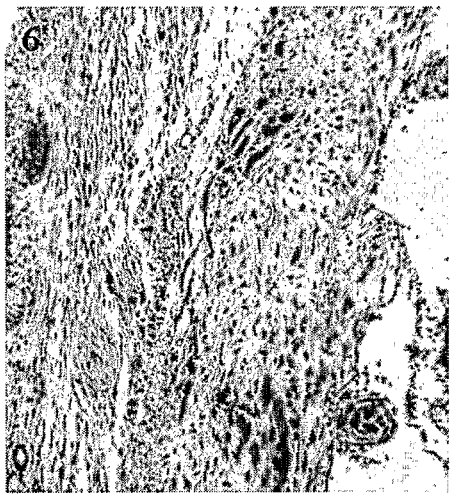
Figure 5:
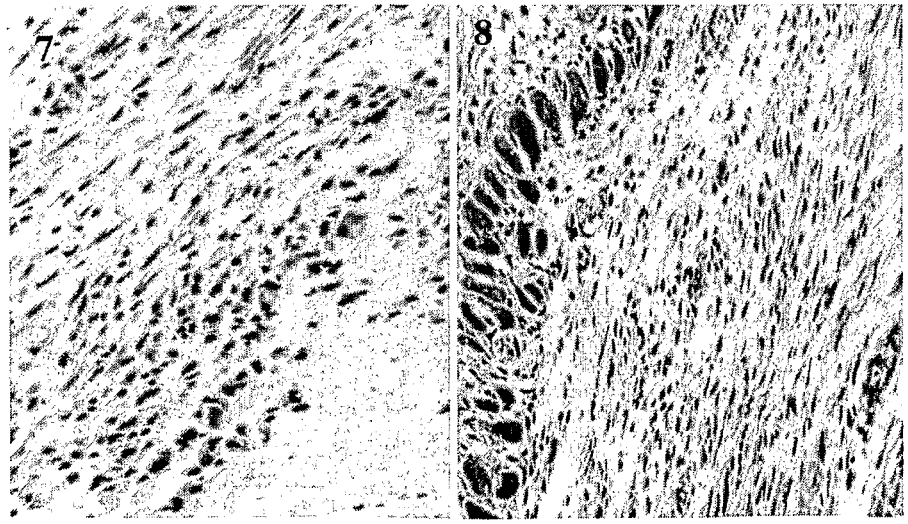

IV. Direct Therapeutic Effects in MI Model without Pretreating MSCs and Transplantation Referring to FIG. 5, following direct local injection of CMF in MI model, it was found two weeks post infarction that in the control group (without CMF treatment) the myocardium on the distal part of the ligation site became substantially white on visual inspection due to ischemic necrosis (FIG. 5: 2). By contrast, the equivalent part in CMF-treated hearts were relatively red in appearance probably due to neovascularization (FIG. 5: 1), which was comparable to the non-ischemic parts of the heart and the sizes of infarct were significantly smaller than those in the control hearts (FIG. 5: 2). Moreover, on transect of the infarct area, the left ventricle walls of the CMF treated hearts (FIG. 5: 3) were significantly thicker than those in control hearts (FIG. 5: 4). Histological observations revealed that the infarct sizes in CMF-treated hearts (n=8) were on average approximately ⅓-½ times smaller than those in the control hearts (n=8), as was calculated by measuring the infarct volume in the left ventricular free wall on day 14 after ligation. By Masson's Trichrome staining, it was found that in CMF treated hearts, myocyte-like cell clusters, which were arranged in almost the same orientation as the infarcted myocardium or the neighboring viable myocardia, were distributed in most parts of the whole infarct regions (FIG. 5: 5). By contrast, the infarcted regions in control hearts were almost completely occupied by fibrous tissue replacement, leaving almost no space for any possible cardiomyocytes regeneration, if any (FIG. 5: 6). Under a higher power field, in a sharp contrast to the overall blue stained fibrous scar in control group (FIG. 5: 8), the whole infarct areas in the CMF treated group were filled with regenerating myocyte clusters, well shaped to bear myocardial morphology with little fibrous tissue in between (FIG. 5: 7), although the sizes of these regenerating myocytes were smaller than the neighboring preexisting myocytes, probably because they were still on the way of maturing.

Furthermore, echocardiography demonstrated that the replacement of infarcted heart tissue with structurally integrated regenerating myocardia and reconstituted vasculatures was accompanied by significant functional improvement by day 2 post-infarct in CMF-treated hearts, and further improvement by day 14 compared with control hearts, probably due to the growth and maturation of the regenerated myocardia and vasculatures that repaired the infarct.

Therapeutic Effect Via Conditioned Medium Induced by CMF-treated MSCs

Figure 6:
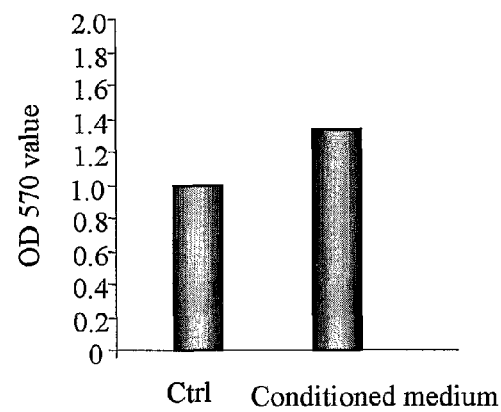
FIG. 6 shows the enhanced proliferation of cultured MSCs and myocardial regeneration induced by conditioned medium.
Figure 6:
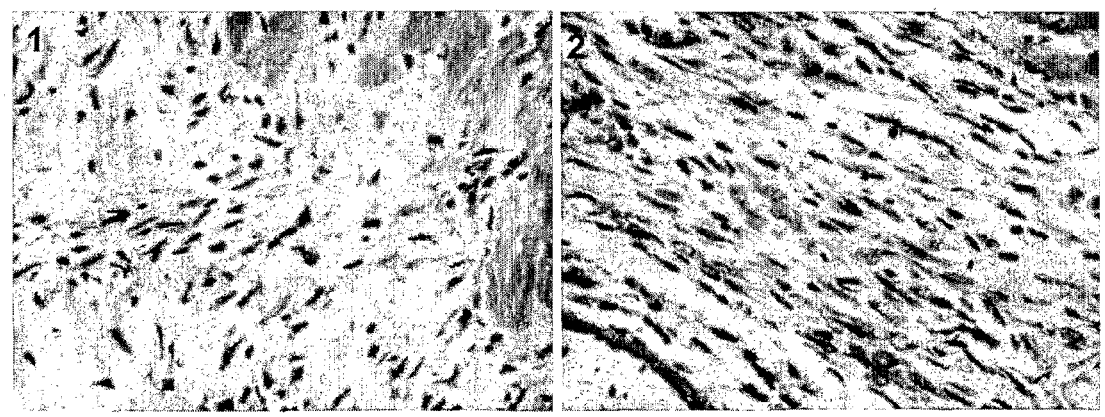

To determine whether conditioned medium containing certain induced proteins secreted by CMF-activated-MSCs would bring about similar effects as CMF direct application or transplantation of the CMF-pretreated-MSCs to the infarct area, the conditioned medium was tested with both MSCs culture and heart infarction animal model. Referring to FIG. 6a, after treatment with conditioned medium for 24 hrs, the proliferation rate of MSCs increased to 120% compared to control medium (fresh growth medium). Referring to FIG. 6b, local injection of conditioned medium to the ischemic region of MI model, cardiomyocyte regeneration was observed. Briefly, many regenerating cardiomyocytes and many newly formed vessels filled with blood cells were observed in the whole infarct zone (FIG. 6b: 2) compared with the fibrous replacement in control (FIG. 6b: 1).

V. Cellular Origin of the Regenerated Myocardia after Direct CMF Treatment

Figure 7:
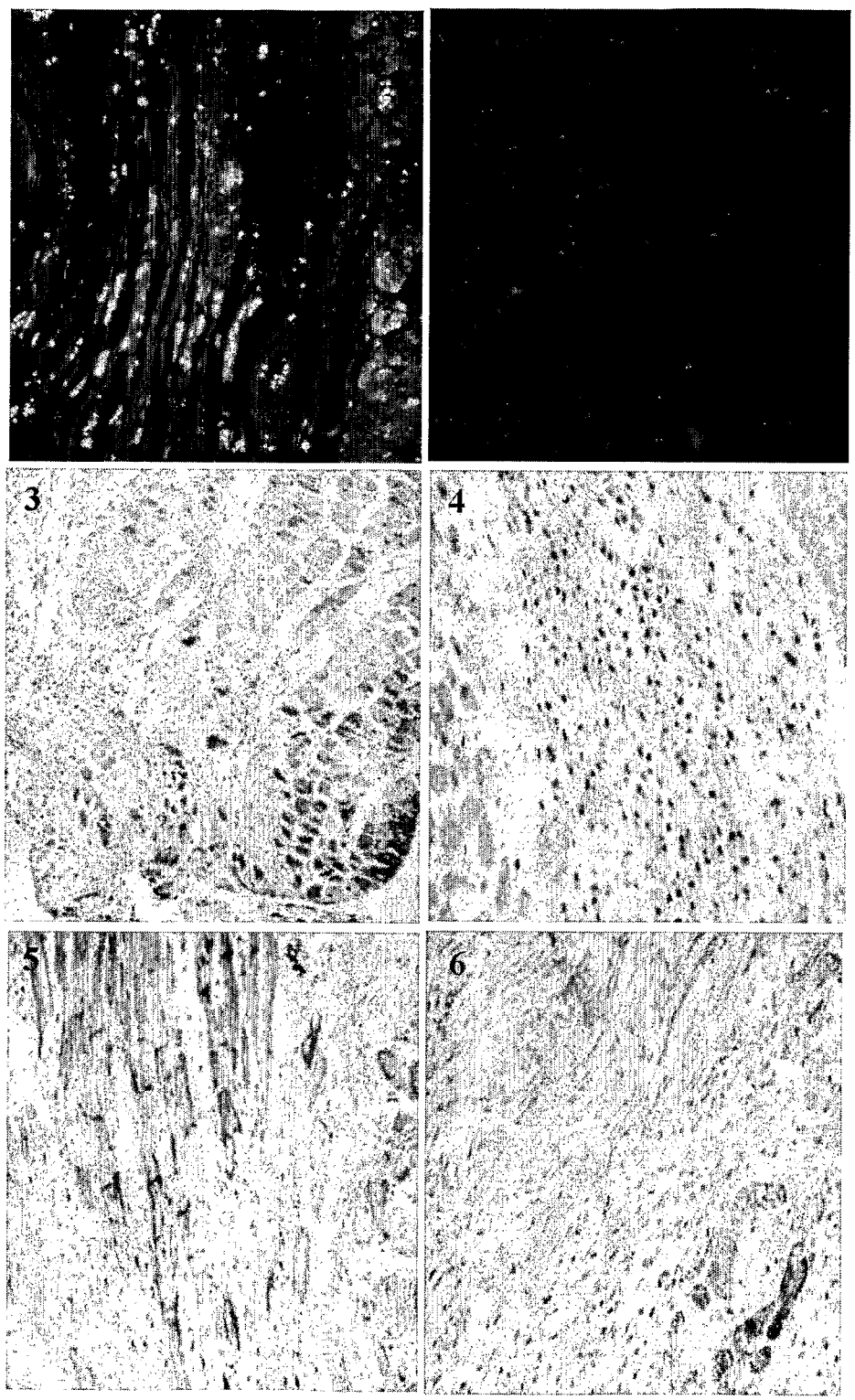
FIG. 7 shows the cellular source for CMF-induced myocardial regeneration in animal MI model.

Referring to FIG. 7, studies on MI model with bone marrow replacement with DiI labeled MSCs have provided direct evidence that the cellular origin of the regenerating myocardium were derived from bone marrow MSCs. One week after bone marrow replacement, heart infarction surgery was performed as described in the above. Fourteen days post infarction, it was found that the whole infarct regions in CMF-treated hearts were well occupied by DiI labeled cells, which were largely absent in any non-infarcted regions of having the preexisting viable cardiomyocytes. These DiI positive cells were clustered together bearing myocardial-like morphology, but smaller in size compared with pre-existing cardiomyocytes (FIG. 7: 1). By contrast, only a few scattered DiI positive cells were observed along the infarct border zone in control infarcted hearts (FIG. 7: 2). To confirm that these well organized DiI positive cells were regenerating myocardia, immunohistochemistry with antibodies specific to troponin I and PCNA were performed. It was found that numerous DiI positive cells distributed in the whole infarct zone were positively stained by specific antibodies for troponin I (FIG. 7: 3) or PCNA (FIG. 7: 4). These DiI and troponin I or PCNA positively stained cells were organized into myocardial-like tissue in the whole infarct zone in CMF treated hearts (FIG. 7: 3 & 4). Under higher power field, these regenerating myocardial-like tissues showed the typical morphology of myocardium with clear intercalated disk connection between regenerating myocytes, indicating the ultrastructural maturation of the individual regenerating myocyte into integrated myocardium (FIG. 7: 5). Without the structural integration between the regenerating myocytes, and between the regenerating myocardium and pre-existing viable myocardium, functional integration and synchronous mechanical activity would not be guaranteed. These regenerating myocardia occupied averagely 69.3% of the total infarct volume on day 14 post-infarct. By contrast, in 6 control hearts, only a few cells were both troponin I and DiI positive and were scattered around the vessels while the infarction zone was mainly occupied by fibrous scar (FIG. 7: 6). These results demonstrated that the CMF induced regenerating myocardium was functional and derived from bone marrow MSCs.

IV Manufacturing Pharmaceutical Compositions and Their Uses in Treating Ischemic Heart Diseases in Mammals Once the effective chemical compound is identified and partially or substantially pure preparations of the compound are obtained either by isolating the compound from natural resources such as plants or by chemical synthesis, various pharmaceutical compositions or formulations can be fabricated from partially or substantially pure compound using existing processes or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more processes established in the industry to the practice of the present invention. Alternatively, people of ordinary skill in the art may modify the existing conventional processes to better suit the compounds of the present invention. For example, the patent or patent application databases provided at USPTO official website contain rich resources concerning making pharmaceutical formulations and products from effective chemical compounds. Another useful source of information is Handbook of Pharmaceutical Manufacturing Formulations, edited by Sarfaraz K. Niazi and sold by Culinary & Hospitality Industry Publications Services.

As used in the instant specification and claims, the term "plant extract" means a mixture of natural occurring compounds obtained from parts of a plant, where at least 10% of the total dried mass is unidentified compounds. In other words, a plant extract does not encompass an identified compound substantially purified from the plant. The term "pharmaceutical excipient" means an ingredient contained in a drug formulation that is not a medicinally active constituent. The term "an effective amount" refers to the amount that is sufficient to elicit a therapeutic effect on the treated subject. Effective amount will vary, as recognized by those skilled in the art, depending on the types of diseases treated, route of administration, excipient usage, and the possibility of co-usage with other therapeutic treatment. A person skilled in the art may determine an effective amount under a particular situation.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

REFERENCES

1. Orlic, D. et al. Bone marrow cells regenerate infarcted myocardium. *Nature* 410, 701-5 (2001).
2. Toma, C., Pittenger, M. F., Cahill, K. S., Byrne, B. J. & Kessler, P. D. Human mesenchymal stem cells differentiate to a cardiomyocyte phenotype in the adult murine heart. *Circulation* 105, 93-8 (2002).
3. Tomita, S. et al. Autologous transplantation of bone marrow cells improves damaged heart function. *Circulation* 100, 11247-56 (1999).
4. Beltrami, A. P. et al. Evidence that human cardiac myocytes divide after myocardial infarction. *N Engl J Med* 344, 1750-7 (2001).
5. Kajstura, J. et al. Myocyte proliferation in end-stage cardiac failure in humans. *Proc Natl Acad Sci USA* 95, 8801-5 (1998).
6. Laugwitz, K. L. et at. Postnatal isl1+ cardioblasts enter fully differentiated cardiomyocyte lineages. *Nature* 433, 647-53 (2005).
7. Leferovich, J. M. et al. Heart regeneration in adult MRL mice. *Proc Natl Acad Sci USA* 98, 9830-5 (2001).
8. Poss, K. D., Wilson, L. G. & Keating, M. T. Heart regeneration in zebrafish. *Science* 298, 2188-90 (2002).
9. Reinecke, H., Zhang, M., Bartosek, T. & Murry, C. E. Survival, integration, and differentiation of cardiomyocyte grafts: a study in normal and injured rat hearts. *Circulation* 100, 193-202 (1999).
10. Taylor, D. A. et al. Regenerating functional myocardium: improved performance after skeletal myoblast transplantation. *Nat Med* 4, 929-33 (1998).
11. Yoo, K. J. et al. Heart cell transplantation improves heart function in dilated cardiomyopathic hamsters. *Circulation* 102, 111204-9 (2000).
12. Mangi, A. A. et al. Mesenchymal stem cells modified with Akt prevent remodeling and restore performance of infarcted hearts. *Nat Med* 9, 1195-201 (2003).

What is claimed is:

1. A method of regenerating myocytes or myocardia in the heart of a mammalian subject suffering from an injured heart muscle, comprising a step of administering an effective amount of a compound in a substantially pure form isolated from natural resources or obtained by chemical synthesis of the following formula:

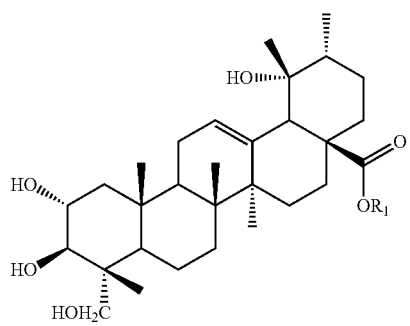

wherein $R_1$ is H or

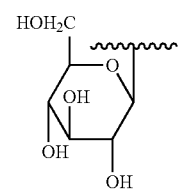

to said subject.

2. The method of claim 1, wherein said injured heart muscle is caused by an ischemic event.

3. The method of claim 2, wherein said ischemic event is myocardial infarction.

4. The method of claim 1, wherein said myocytes or myocardia are regenerated by one or more of (a) increasing viability of myogenic precursor cells to enable said precursor cells to survive through an absolute ischemic period;
   (b) reconstituting a damaged blood supply network in said heart region where said inured muscle is located; and (c) enhancing cardiomygenic differentiation efficiency of said precursor cells down cardiac linage, said steps being performed simultaneously or in any particular order.

5. The method of claim 4, wherein said myogenic precursor cells are mesenchymal stem cells coming from bone marrow through blood circulation.

6. The method of claim 1, further comprising the steps of: (a) formulating said compound into a dosage form and (b) systemically administering said compound in said dosage form to said mammalian subject.

7. The method of claim 6, wherein said dosage form is selected from the group consisting of tablet, capsule, injection solution, syrup, suspension and powder.

\* \* \* \* \*